(12) United States Patent  
Landers

(10) Patent No.: US 11,516,994 B1  
(45) Date of Patent: *Dec. 6, 2022

(54) ANIMAL SENSORY STIMULATION WITH FUR DIFFERENTIAL IMPEDANCE DETECTION

(71) Applicant: GPSip, Inc., Oshkosh, WI (US)

(72) Inventor: Rodney P. Landers, Stillwater, MN (US)

(73) Assignee: GPSip, Inc., Oshkosh, WI (US)

( * ) Notice: Subject to any disclaimer, the term of this patent is extended or adjusted under 35 U.S.C. 154(b) by 31 days.

This patent is subject to a terminal disclaimer.

(21) Appl. No.: 17/152,781

(22) Filed: Jan. 19, 2021

Related U.S. Application Data

(63) Continuation-in-part of application No. 16/854,892, filed on Apr. 21, 2020, now Pat. No. 10,893,662, which is a continuation-in-part of application No. 16/237,375, filed on Dec. 31, 2018, now Pat. No. 10,624,319, which is a continuation-in-part of application No. 14/662,232, filed on Mar. 18, 2015, now Pat. No. 10,165,756.

(60) Provisional application No. 61/954,598, filed on Mar. 18, 2014.

(51) Int. Cl.
| | |
|---|---|
| *A01K 15/02* | (2006.01) |
| *A01K 27/00* | (2006.01) |
| *A01K 11/00* | (2006.01) |
| *G01N 27/22* | (2006.01) |
| *A61N 1/36* | (2006.01) |
| *A61N 1/38* | (2006.01) |

(52) U.S. Cl.
CPC .......... *A01K 15/023* (2013.01); *A01K 11/008* (2013.01); *A01K 27/001* (2013.01); *G01N 27/228* (2013.01); *A61N 1/36028* (2013.01); *A61N 1/36031* (2017.08); *A61N 1/38* (2013.01)

(58) Field of Classification Search
CPC ........ A01K 15/00; A01K 15/02; A01K 11/00; A01K 11/006; A01K 11/008
See application file for complete search history.

(56) References Cited

U.S. PATENT DOCUMENTS

| | | | | |
|---|---|---|---|---|
| 5,046,453 A | * | 9/1991 | Vinci ................... | A01K 15/022 239/152 |
| 5,568,119 A | * | 10/1996 | Schipper ................ | G08B 21/22 379/38 |
| 6,232,880 B1 | * | 5/2001 | Anderson ............ | A01K 15/023 340/573.3 |
| 6,271,757 B1 | * | 8/2001 | Touchton ............. | A01K 15/023 119/908 |
| 9,226,479 B2 | * | 1/2016 | Bianchi ................ | A01K 11/008 |

(Continued)

*Primary Examiner* — Monica L Perry  
*Assistant Examiner* — Aaron M Rodziwicz  
(74) *Attorney, Agent, or Firm* — Albert W. Watkins

(57) ABSTRACT

A collar-mounted location sensor and stimulation unit includes a body. A generally planar stimulation unit and differential impedance-based fur detector in combination protect the animal from harmful stimulation. At least one sensory stimulator is configured to provide at least one of auditory, kinesthetic, and visual stimulation responsive to an output of a location sensor. One or more of a voltage, current, oscillation frequency, extent of modulation, or other output characteristic of the stimulation unit output is varied responsive to the detected fur differential impedance to protect and benefit both the body and mind of the animal.

18 Claims, 5 Drawing Sheets

(56) References Cited

U.S. PATENT DOCUMENTS

| | | | | |
|---|---|---|---|---|
| 2001/0026240 | A1* | 10/2001 | Neher | G01S 19/16 |
| | | | | 342/357.75 |
| 2002/0196151 | A1* | 12/2002 | Troxler | G08B 21/0269 |
| | | | | 340/573.3 |
| 2004/0196182 | A1* | 10/2004 | Unnold | G08B 21/0269 |
| | | | | 342/357.25 |
| 2006/0027185 | A1* | 2/2006 | Troxler | G01C 21/005 |
| | | | | 119/721 |
| 2008/0162034 | A1* | 7/2008 | Breen | G01C 21/3461 |
| | | | | 701/533 |
| 2008/0246656 | A1* | 10/2008 | Ghazarian | G08B 13/1427 |
| | | | | 455/343.2 |
| 2013/0157628 | A1* | 6/2013 | Kim | A01K 15/04 |
| | | | | 455/414.1 |
| 2013/0307688 | A1* | 11/2013 | Hoffman | G08B 25/08 |
| | | | | 340/539.13 |
| 2014/0251233 | A1* | 9/2014 | Bianchi | A01K 15/021 |
| | | | | 119/720 |
| 2015/0040839 | A1* | 2/2015 | Goetzl | A01K 15/021 |
| | | | | 119/720 |

* cited by examiner

ANIMAL SENSORY STIMULATION WITH FUR DIFFERENTIAL IMPEDANCE DETECTION

CROSS REFERENCE TO RELATED APPLICATIONS

This application is a Continuation-In-Part of U.S. patent application Ser. No. 16/854,892 filed Apr. 21, 2020 and granted as U.S. Pat. No. 10,893,662 on Jan. 19, 2021 and herewith, which is a Continuation-In-Part of U.S. patent application Ser. No. 16/237,375 filed Dec. 31, 2018 and granted as U.S. Pat. No. 10,624,319 on Apr. 21, 2020, which is a Continuation-In-Part of U.S. patent application Ser. No. 14/662,232 filed Mar. 18, 2015 and granted as U.S. Pat. No. 10,165,756 on Jan. 1, 2019, which in turn claims the benefit under 35 U.S.C. 119(e) of U.S. provisional 61/954,598, filed Mar. 18, 2014, the teachings and entire contents of each which are incorporated herein by reference in entirety.

BACKGROUND OF THE INVENTION

1. Field of the Invention

This invention pertains generally to electrical communications, and more particularly to condition responsive indicating systems with a radio link and including personal portable device for tracking location. The condition responsive indicating systems of the present invention monitor the specific condition of humans or animals. In one preferred manifestation, a fully self-contained collar designed in accord with the teachings of the present invention monitors the location of a pet such as a dog, and provides well defined and positive stimulus to train the pet to stay within a predetermined area.

2. Description of the Related Art

Dogs are well known as "man's best friend" owing to the many beneficial services that they provide. However, and likely since mankind first befriended dogs, there has existed a need to control the territory that a dog has access to. There are many reasons that motivate this need, many which may be relatively unique to a particular dog or owner, and other reasons that are far more universal.

Irrespective of the reason, there have been limited ways to communicate to a dog a territory that the dog should stay within, and to elicit this behavior from a dog. One method is a fixed containment structure such as a fence or building. A structure of this nature provides a physical boundary or barrier which blocks passage of an animal such as a pet or farm animal. As may be apparent, such structures are typically expensive and time consuming to install, and necessarily static in location. In other words, they are only useful at the location where they are constructed, and so are of no value when a pet and owner travel. Furthermore, these static structures often interfere in other ways with other activities of the dog owner, such as with lawn care or interfering with the owner's movement about a property. In addition, a dog may find ways to bypass the structure, such as by digging under a fence or slipping through a not-quite-completely secured gate.

A second approach to controlling accessible territory is through a combination collar and leash or similar restraint. The leash is anchored to a fixed point, or in the best of situations, to a line or cable along which the dog can travel. Unfortunately, most dogs are notoriously bad at untangling or unwrapping a leash from a fixed object. Consequently, dogs tend to tangle the leash about trees, posts, and other objects, and can become completely unable to move. If the owner is not aware that the dog has become tangled, this can lead to dangerous situations in cases such as extreme weather or when the dog has been left unattended for an extended period.

Additionally, some dogs are very good at escaping the leash, such as by backing away from the leash and using the leash force to slip off the collar, or by chewing through the leash. Once again, if the owner is unaware, the dog may travel from the desired area into other unsuitable areas such as roadways and the like. This may put both dog and humans in jeopardy, such as when a vehicle swerves to avoid the dog or when a dog has a temperament not suited to the general human population.

The leash also necessarily defines the region in which the dog may travel. For exemplary purposes, with a ground stake and a leash the dog is constrained to a circle. In this example, the owner will typically define the circle to the smallest radius that the dog may desirably travel within. As can be understood, for all but circularly shaped areas, this leads to a great deal of space that the dog cannot access, but which would otherwise be suitable for the dog.

In consideration of the limitations of static structures and leashes, various artisans have proposed other systems that provide more flexibility and capability, such as buried or above ground transmitter antennas and radio collars that either detect the crossing of a buried line or detect the reception or absence of reception of a signal broadcast by the transmitter antenna. When an undesirable location is detected, the radio collar is then triggered, typically to provide a painful electrical stimulation to the dog. Desirably, the electrical stimulation is mild enough not to harm the dog, but yet still strong enough to cause the dog to want to avoid additional similar stimulation. These systems remove the physical link between a dog and a static structure, meaning the dog will not get tangled in obstacles when moving about. Further, in the case of a buried line, the line may follow any geometry of land, and so is not limited to a circular pattern limited by a particular radius.

Unfortunately, burying a line can be difficult or impossible if there are other objects, such as irrigation systems, buried utility lines, landscaping, hard surfaces, trees, or other fixed objects. Additionally, current soil conditions such as frozen soil or snow-covered ground in the winter may also limit the ability to bury the line. Furthermore, the effort required to bury the line limits these systems to a single location, meaning the system cannot readily be moved or transposed from the home to a popular park or the like.

Radio systems that rely upon the detection of a signal to generate a shock, such as the buried line, are also well known to be significantly affected by static and other forms of Electro-Magnetic Interference or Radio-Frequency Interference (EMI-RFI). Consequently, a dog may be shocked or otherwise punished without basis or appropriate reason. This problem is also very location dependent, meaning that there are places where there is so much EMI-RFI that a radio system is completely unusable. As a result of the inability to completely eliminate or substantially eradicate the effects of EMI-RFI, the use of these radio systems is far from universal.

When the shock is instead triggered by the absence of a radio signal, such as when a beacon is used to contain a pet, obstacles such as buildings may prevent reception, undesirably limiting the range of travel of the animal. Furthermore, blocking the signal from the collar, such as when a dog lays down, is being caressed by the owner, or is oriented in the wrong direction, may also lead to radio signal attenuation and undesirable triggering of the shock.

As is known in the field of psychology, this random punishment that is commonplace in both types of radio systems can literally destroy the training of a dog, and may lead to erratic or wanton misbehavior. Instead, many dog owners continue to rely upon static structures or leashes to control the territory accessible by their dog.

Another problem arises when a dog unintentionally crosses a buried line. Since it is the crossing of the line that leads to the stimulation, even when the dog realizes and tries to return, the same stimulation originally keeping the dog in a containment area is now being used to keep the dog out of that containment area. Consequently, the dog will be extremely confused, and will commonly not return, even where the dog would have otherwise. As but one exemplary purpose, when a rabbit, squirrel, or other animate creature is being chased by the dog, the dog will typically be so intent on the pursuit as to completely lose track of the location of the buried line. The dog's speed may be so great that even the stimulation is very short as the dog crosses the buried line, in the heat of the chase. Furthermore, the dog's attention and focus are thoroughly directed at the pursuit of the animate creature, and even the most powerful stimulus may go unnoticed. However, once the chase is over, the dog's adrenaline or drive has diminished. A reasonably well-behaved dog will then most likely be moving more slowly back toward "home" within the containment area. Unfortunately then, the stimulation trying to re-enter will most frequently be of much longer duration, and much more recognized by the now not-distracted dog, than when the dog left the containment area. As can be appreciated, this is backwards of the intent of a training system.

With the advent and substantial advancement of Global Positioning Systems (GPS), presently primarily used for navigation, artisans have recognized the opportunity to incorporate GPS technology into pet containment. Several systems have been proposed in the literature for several decades, but these systems have not as yet become commercially viable.

One significant limitation of prior art GPS systems is the accuracy of the system. Accuracy can be dependent upon variables such as atmospheric variations, signal reflections and signal loss due to obstacles, and variability intentionally introduced into the system. Similar variability is found in various radio and cellular locating systems.

A GPS or similar navigation system that is accurate to plus or minus ten meters is very adequate for navigational purposes, for example to guide a person to a commercial building for a meeting or for other commerce. However, for pet containment this level of accuracy is completely unacceptable. For exemplary purposes, many residential yards are forty feet wide, or approximately 10 meters. A system that is only accurate to plus or minus ten meters might try to locate the dog in either neighbor's yard on any given day or at any given moment, depending upon unpredictable and uncontrollable variables such as atmospheric conditions. As will be readily appreciated, this unpredictable locating will lead to punishment of the animal when, in fact, the animal is within the proper location. In turn, this will lead to a complete failure of training, and erratic and unpredictable behavior of the animal.

Another limitation is the amount of calculation required to determine whether the pet is within a selected area of containment. Most prior art GPS systems use nodes to define the perimeter, and then mathematically calculate where the pet is relative to the nodes. Unfortunately, this requires a substantial amount of computation, which increases greatly as the number of nodes are increased. As a result, these systems commonly rely upon a primary processing system that is remote from the dog, to which the dog's collar is coupled via radio waves or the like. This permits the primary processing system to perform calculations and then relay results or control signals back to the collar. Undesirably, this also adds complexity, drains precious battery power limiting the usable collar time, and again makes the containment system dependent upon conventional radio communications systems. In addition, the need for both the collar and a secondary base station makes the system far less portable. This means, for example, that taking the dog away from home to a park may be impractical.

A further limitation of the prior art is battery life. A collar that must be removed and recharged every few hours is unacceptable for most purposes. Unfortunately, the intensive computations required by prior art systems require either a fast and consequently higher power processor unit, or a communications link such as a radio link to a base station. While the collar unit may transmit data back to the base unit to avoid the need for complex computational ability, even the transmission of position information and reception of collar actions requires a reasonably powered radio. It will be apparent that walkie-talkies, cell phones and other hand-held radio devices all have very large batteries to provide adequate transmission and reception life, and yet these devices often only support several hours of communications. As can be appreciated, size and weight are severely restricted for a device fully self-contained on a dog's collar, and the inclusion of a large battery is undesirable.

Yet another limitation of the prior art is the unintentional blocking or loss of GPS signals. There are a number of conditions that can lead to loss of GPS signals. One is unfavorable weather, which can lead to a severely attenuated satellite signal, and much higher Signal to Noise Ratios (SNR). Another condition is an adjacent building, canyon wall, or other obstacle that blocks satellite signals. Such a signal might, for exemplary purposes, either block all signals such as commonly occurs within a building, or instead may only block signals from one direction. However, GPS systems require multiple satellites to obtain a position fix, and even if only one of the satellites is blocked, then the ability to accurately fix position may be lost. Another situation that can lead to signal loss is when the collar itself is covered. This can, for exemplary and non-limiting purposes, occur when a dog lays down. If the dog lays in an unfortunate position partially or completely covering the collar, then satellite signals will be either blocked or too severely attenuated.

In any of these situations where the GPS signal is partially or completely blocked or attenuated, the latitudinal and longitudinal positional accuracy will either be inadequate, or may be completely lost. In such instances, a prior art collar may become completely non-functional. Worse, this loss of function can occur without notice in an erratic manner, possibly causing severe harm to the training of the dog.

In addition to the aforementioned limitations, prior art electronic fences have also attempted to train the animal using punishment, such as a shock, to elicit the desired behavior. As is very well known and established, negative reinforcement is less effective than positive reinforcement or a combination of positive and negative reinforcement. Furthermore, the type of reinforcement can also affect the temperament of the animal Consequently, it is desirable to not only provide consistent behavioral reinforcement, but also to provide that reinforcement in a positive manner.

Another significant limitation of prior art systems is the size and complexity of the various pet containment systems. As a result, the prior art pet-worn containment units often require their own mounting or coupling to the pet, which may prevent a pet owner from using a particularly preferred or well-fitting collar. In other instances, the mounting itself is sufficiently complex to discourage pet owners from coupling the collar unit to the collar.

In addition, the stimulation is typically provided through a high voltage pulse applied across two prongs that are pressed into the neck of the pet. Since many animals have a relatively thick base coat, in many cases this also requires a tight collar to reliably couple the prongs into the dog. Unfortunately, if the collar is left on for extended periods, as it would desirably be for most pets, this force, any electrical stimulation, and ordinary movement of the pet will all combine to lead to gradual tissue necrosis. This can and has led to deep sores or pockets of disease within the pet's neck, which is highly inhumane and can seriously adversely affect the health and well-being of the pet.

The risk of tissue necrosis can be exacerbated by known variability amongst animals in skin, hair, and fur health and electrical characteristics. These risks can arise from extremely transitory events and environmental exposures and conditions, for exemplary purposes including momentary extreme biological changes arising from a chase. Such highly transitory events and the biological changes relevant to skin, hair, and fur health and electrical characteristics may only last seconds or minutes. Other events, exposures and conditions may still be transitory, but may last for longer periods. Food, hydration, and activities such as a plunge in a salt-water body may alter skin, hair, and fur health and electrical characteristics for hours or days, and changes due to weather may similarly last for hours or days, and may further include seasonal variations. Longer term changes can arise from changes in fat deposits, animal age, medications, and the like. Finally, other variability amongst animals in skin, hair, and fur health and electrical characteristics may be very interminable, for exemplary purposes due to genetic variations derived from species, subspecies, and individual animal genetics. The consequence of this variability of skin, hair and fur health and electrical characteristics, and the inability in the prior art to adequately compensate for such variability in spite of best and even exceptional effort by many highly skilled artisans, has meant that even a very careful and conscientious pet owner may still discover significant harm has been purveyed by manufacturers and sellers of the prior art two-prong shock collar.

The following patents and published patent applications are believed to be exemplary of the most relevant prior art, and the teachings and contents of each are incorporated herein by reference: U.S. Pat. No. 4,393,448 by Dunn et al, entitled "Navigational plotting system"; U.S. Pat. No. 4,590,569 by Rogoff et al, entitled "Navigation system including an integrated electronic chart display"; U.S. Pat. No. 4,611,209 by Lemelson et al, entitled "Navigation warning system and method"; U.S. Pat. No. 4,817,000 by Eberhardt, entitled "Automatic guided vehicle system"; U.S. Pat. No. 4,999,782 by BeVan, entitled "Fixed curved path waypoint transition for aircraft"; U.S. Pat. No. 5,067,441 by Weinstein, entitled "Electronic assembly for restricting animals to defined areas"; U.S. Pat. No. 5,191,341 by Gouard et al, entitled "System for sea navigation or traffic control/assistance"; U.S. Pat. No. 5,351,653 by Marischen et al, entitled "Animal training method using positive and negative audio stimuli"; U.S. Pat. No. 5,353,744 by Custer, entitled "Animal control apparatus"; U.S. Pat. No. 5,355,511 by Hatano et al, entitled "Position monitoring for communicable and uncommunicable mobile stations"; U.S. Pat. No. 5,381,129 by Boardman, entitled "Wireless pet containment system"; U.S. Pat. No. 5,389,934 by Kass, entitled "Portable locating system"; U.S. Pat. No. 5,408,956 by Quigley, entitled "Method and apparatus for controlling animals with electronic fencing"; U.S. Pat. No. 5,450,329 by Tanner, entitled "Vehicle location method and system"; U.S. Pat. No. 5,568,119 by Schipper et al, entitled "Arrestee monitoring with variable site boundaries"; U.S. Pat. No. 5,587,904 by Ben-Yair et al, entitled "Air combat monitoring system and methods and apparatus useful therefor"; U.S. Pat. No. 5,594,425 by Ladner et al, entitled "Locator device"; U.S. Pat. No. 5,751,612 by Donovan et al, entitled "System and method for accurate and efficient geodetic database retrieval"; U.S. Pat. No. 5,791,294 by Manning, entitled "Position and physiological data monitoring and control system for animal herding"; U.S. Pat. No. 5,857,433 by Files, entitled "Animal training and tracking device having global positioning satellite unit"; U.S. Pat. No. 5,868,100 by Marsh, entitled "Fenceless animal control system using GPS location information"; U.S. Pat. No. 5,911,199 by Farkas et al, entitled "Pressure sensitive animal training device"; U.S. Pat. No. 5,949,350 by Girard et al, entitled "Location method and apparatus"; U.S. Pat. No. 6,043,748 by Touchton et al, entitled "Satellite relay collar and programmable electronic boundary system for the containment of animals"; U.S. Pat. No. 6,114,957 by Westrick et al, entitled "Pet locator system"; U.S. Pat. No. 6,172,640 by Durst et al, entitled "Pet locator"; U.S. Pat. No. 6,232,880 by Anderson et al, entitled "Animal control system using global positioning and instrumental animal conditioning"; U.S. Pat. No. 6,232,916 by Grillo et al, entitled "GPS restraint system and method for confining a subject within a defined area"; U.S. Pat. No. 6,236,358 by Durst et al, entitled "Mobile object locator"; U.S. Pat. No. 6,263,836 by Hollis, entitled "Dog behavior monitoring and training apparatus"; U.S. Pat. No. 6,271,757 by Touchton et al, entitled "Satellite animal containment system with programmable Boundaries"; U.S. Pat. No. 6,313,791 by Klanke, entitled "Automotive GPS control system"; U.S. Pat. No. 6,421,001 by Durst et al, entitled "Object locator"; U.S. Pat. No. 6,441,778 by Durst et al, entitled "Pet locator"; U.S. Pat. No. 6,480,147 by Durst et al, entitled "Portable position determining device"; U.S. Pat. No. 6,487,992 by Hollis, entitled "Dog behavior monitoring and training apparatus"; U.S. Pat. No. 6,518,919 by Durst et al, entitled "Mobile object locator"; U.S. Pat. No. 6,561,137 by Oakman, entitled "Portable electronic multi-sensory animal containment and tracking device"; U.S. Pat. No. 6,581,546 by Dalland et al, entitled "Animal containment system having a dynamically changing perimeter"; U.S. Pat. No. 6,700,492 by Touchton et al, entitled "Satellite animal containment system with programmable boundaries"; U.S. Pat. No. 6,748,902 by Boesch et al, entitled "System and method for training of animals"; U.S. Pat. No. 6,903,682 by Maddox, entitled "DGPS animal containment system"; U.S. Pat. No. 6,923,146 by Kobitz et al, entitled "Method and apparatus for training and for constraining a subject to a specific area"; U.S. Pat. No. 7,034,695 by Troxler, entitled "Large area position/proximity correction device with alarms using (D)GPS technology"; U.S. Pat. No. 7,259,718 by Patterson et al, entitled "Apparatus and method for keeping pets in a defined boundary having exclusion areas"; U.S. Pat. No. 7,328,671 by Kates, entitled "System and method for computer-controlled animal toy"; U.S. Pat. No. 7,677,204 by James, entitled "Dog training device"; U.S. Pat. No. 8,155,871 by Lohi et al, entitled "Method, device, device arrangement and computer program for tracking a moving object"; U.S. Pat. No. 8,115,942 by Thompson et al, entitled "Traveling invisible electronic containment perimeter—method and apparatus"; U.S. Pat. No. 8,624,723 by Troxler, entitled "Position and proximity detection systems and methods"; U.S. Pat. No. 8,757,098 by So et al, entitled "Remote animal training system using voltage-to-frequency conversion"; U.S. Pat. No. 8,797,141 by Best et al, entitled "Reverse RFID location system"; U.S. Pat. No. 8,839,744 by Bianchi et al, entitled "Mobile telephone dog training tool and method"; U.S. Pat. No. 8,851,019 by Jesurum, entitled "Pet restraint system"; 2007/0204804 by Swanson et al, entitled "GPS pet containment system and method"; 2008/0252527 by Garcia, entitled "Method and apparatus for acquiring local position and overlaying information"; 2011/0193706 by Dickerson, entitled "Sensor collar system"; 2012/0000431 by Khoshkish, entitled "Electronic pet containment system"; 2013/0127658 by McFarland et al, entitled "Method and apparatus to determine actionable position and speed in GNSS applications"; and EP 0699330 and WO 94/27268 by Taylor, entitled "GPS Explorer".

Several United States granted patents and US and international patent applications commonly owned with the present invention illustrate a wireless location assisted zone guidance system and various apparatus that provide a number of features and benefits not available in the prior art, including a collar-mounted apparatus that allows users to create unique containment areas in complex shapes with progressive alert zones, and affix the collar to an animal to be trained, monitored, and contained. The collar may operate entirely independent of other terrestrial apparatus for periods greatly extended when compared to the prior art. Exemplary patents, the teachings and contents which are incorporated herein in entirety, include U.S. Pat. Nos. 7,677,204; 9,795,118; 9,961,884; 10,064,390; 10,080,346; 10,165,755; 10,165,756; 10,172,325; 10,251,371; 10,292,365; 10,342,218; 10,405,520; 10,455,810; 10,470,437; 10,624,319; and 10,820,575.

In addition to the foregoing, Webster's New Universal Unabridged Dictionary, Second Edition copyright 1983, is incorporated herein by reference in entirety for the definitions of words and terms used herein.

SUMMARY OF THE INVENTION

In a first manifestation, the invention is a collar-mounted animal sensory stimulation unit with fur differential impedance detection. The animal sensory stimulation unit has a body supporting a first plurality of exposed stimulation electrodes and at least one dielectrically isolated electrode. An electrical stimulation generator has an electrical stimulation output electrically coupled to at least a first one of the plurality of exposed stimulation electrodes. An impedance detector is electrically coupled to at least two of the first plurality of exposed stimulation electrodes and the at least one dielectrically isolated electrode, and is configured to detect exposed electrode impedance between the at least two impedance detector electrodes and measure capacitance at least through the at least one dielectrically isolated electrode. The electrical stimulation generator is configured to alter the electrical stimulation output responsive to the detected exposed electrode impedance and the measured capacitance.

In a second manifestation, the invention is a method of providing electrical animal sensory stimulation through animal fur responsive to differential impedance detection. In accord with the method, stimulation electrodes are electrically coupled to the animal fur. Impedance is measured between the stimulation electrodes. At least one dielectrically isolated electrode is electrically coupled to the animal fur. Capacitance of the animal fur is measured through the at least one dielectrically isolated electrode. The measured impedance and capacitance are determined to represent that the stimulation electrodes are coupled to the animal fur. Responsive to the determining step, electrical stimulation is applied through the stimulation electrodes to the animal fur. Electrical stimulation through the stimulation electrodes to the animal fur is extinguished absent the determining step representing that the stimulation electrodes are coupled to the animal fur.

In a third manifestation, the invention is a method of providing electrical animal sensory stimulation through animal fur responsive to differential impedance detection. In accord with the method, stimulation electrodes are electrically coupled to the animal fur. Impedance is measured between the stimulation electrodes. At least one dielectrically isolated electrode is electrically coupled to the animal fur. Capacitance of the animal fur is measured through the at least one dielectrically isolated electrode. An output of an electrical stimulation generator is varied responsive to the detected magnitude of impedance and the measured capacitance. The electrical animal sensory stimulation is applied through the electrical stimulation electrodes to the animal fur subsequent to the output varying step.

OBJECTS OF THE INVENTION

The present invention and the preferred and alternative embodiments have been developed with a number of objectives in mind. While not all of these objectives are found in or required of every embodiment, these objectives nevertheless provide a sense of the general intent and the many possible benefits that are available from ones of the various embodiments of the present invention.

A first object of the invention is to provide a safe and humane apparatus for modifying the behavior of a pet. From the descriptions provided herein and the teachings incorporated by reference herein above, it will be apparent that the present invention may also be applied in certain instances to humans, livestock or other animals. A second object of the invention is to provide a fully self-contained apparatus that will determine location and provide stimuli based upon that location for extended periods of operation. As a corollary, the fully self-contained apparatus is preferably operational with universally available location systems, including but not limited to satellite GPS, cellular telephone triangulation systems, and radio triangulation system such as Loran, but may alternatively be provided with a custom location system if so desired. By using universally available location systems, there is no limit on the locations where the apparatus may be used. Another object of the present invention is to enable simple and efficient set-up and operation by a person. A further object of the invention is to efficiently and expeditiously train a pet, to significantly reduce training time and increase the effectiveness of the training. As a corollary, embodiments of the present invention will preferably provide the effective animal training while preserving the spirit and positive attitude of the animal Yet another object of the present invention is to enable a person to set an acceptable area or "safe zone" using only the self-contained apparatus, and to adjust or redefine the area again by simple manipulation of the self-contained apparatus. An additional object of the invention is to enable the self-contained apparatus to automatically generate a number of zones that facilitate positive training and behavior modification, and thereby guide a pet or other living being appropriately. A further object of the present invention is to provide electrical stimulation through a much more humane delivery path than prior art two-terminal shock collars. Yet another object of the present invention is to detect when the electrodes are placed on a pet through a reduced energy detection of fur impedance. As a corollary thereto, embodiments of the present invention will not apply electrical stimulation to an animal when the impedance is out of appropriate range, such as for exemplary and non-limiting purpose when the animal is wet from playing in the ocean. An additional object of the invention is to enhance detection sensitivity and identification of animal hair or fur, even when such detection might in the prior art otherwise be hindered by differences in species and breeds, short-term environmental variations in the animal hair or fur, and other factors. An even further object of the present invention is to provide a substantially planar electrode surface having alternating polarity electrodes to better facilitate fur detection and electrical stimulation. An additional object of the invention is to provide a user-removable cover that electrically isolates the electrodes from the animal.

BRIEF DESCRIPTION OF THE DRAWINGS

The foregoing and other objects, advantages, and novel features of the present invention can be understood and appreciated by reference to the following detailed description of the invention, taken in conjunction with the accompanying drawings, in which.

DESCRIPTION OF THE PREFERRED EMBODIMENT

In a preferred embodiment of the invention, a pet owner might want to establish a containment area on an example property. Using the teachings of commonly owned U.S. Pat. Nos. 7,677,204; 9,795,118; 9,961,884; 10,064,390; 10,080,346; 10,165,755; 10,165,756; 10,172,325; 10,251,371; 10,292,365; 10,342,218; 10,405,520; 10,455,810; 10,470,437; 10,624,319; and 10,820,575; the teachings which were incorporated herein above by reference, the collar may be designed to contain an entire and independent pet containment system. In other words, no additional components would need to be purchased or acquired, nor is there a need for any other external device other than the GPS satellites or other suitable location beacons. The collar will interact directly with GPS signals received from GPS satellites or other suitable location beacons as selected by a designer, and may determine latitude and longitude.

In accord with the teachings of these aforementioned and other commonly owned inventions, a comforting stimulus may be provided at particular intervals to assure or reassure the dog. Furthermore, such stimulus may be timed in accord with activity of the dog, such as when the dog is moving about and remaining within the safe zone. In such case, a comforting tone or recorded sound such as the owner's voice saying "good dog" may be periodically generated. In one embodiment contemplated herein, the velocity of the dog, including direction and speed, will also be calculated. In the event there is a danger of the dog moving outside of the safe zone, the comforting stimulus may be withheld, until the dog is confirmed to be remaining in the safe zone.

Additional zones may be identified. For exemplary purposes, these might include a "first alert" zone used to generate a vibration which is preferably very distinct from the comforting tone or "good dog" recording of the safe zone. This will preferably gently alert the dog of the transition out of the safe zone and to the need to return to the safe zone.

A "second alert" zone may be used to trigger an electrical stimulation. In the second alert zone, this stimulation may be relatively mild or medium stimulation.

Finally, at a point outside of the desired containment zone the dog may be stimulated with a stronger electrical stimulation. However, this stimulation will most preferably not continue indefinitely, which would otherwise be recognized to be quite inhumane.

Figure 1:
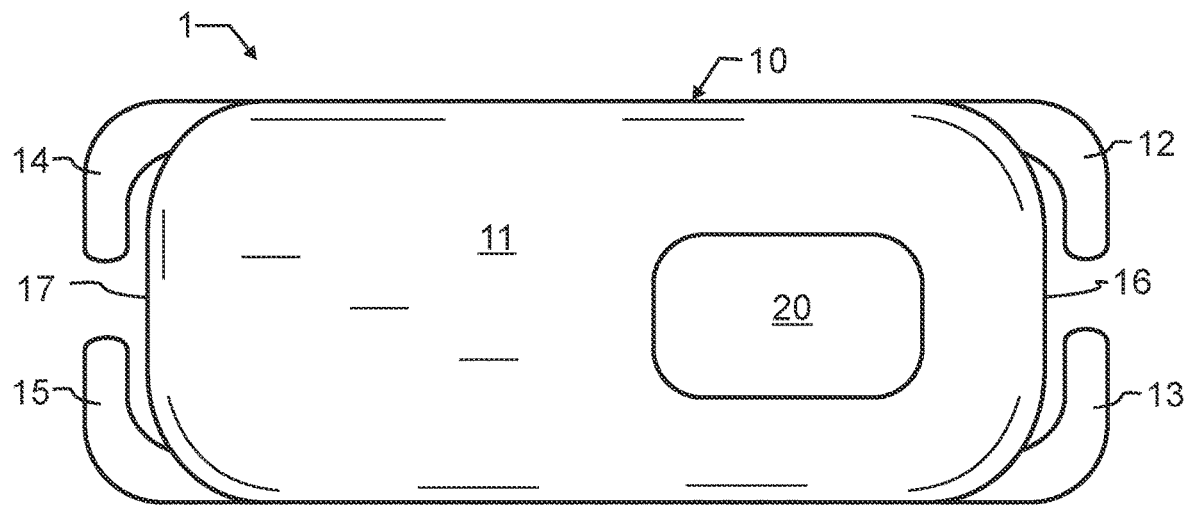
FIG. 1 illustrates a first preferred embodiment collar-mounted location sensor and stimulation unit from a bottom plan view designed in accord with the teachings of the present invention.
Figure 2:
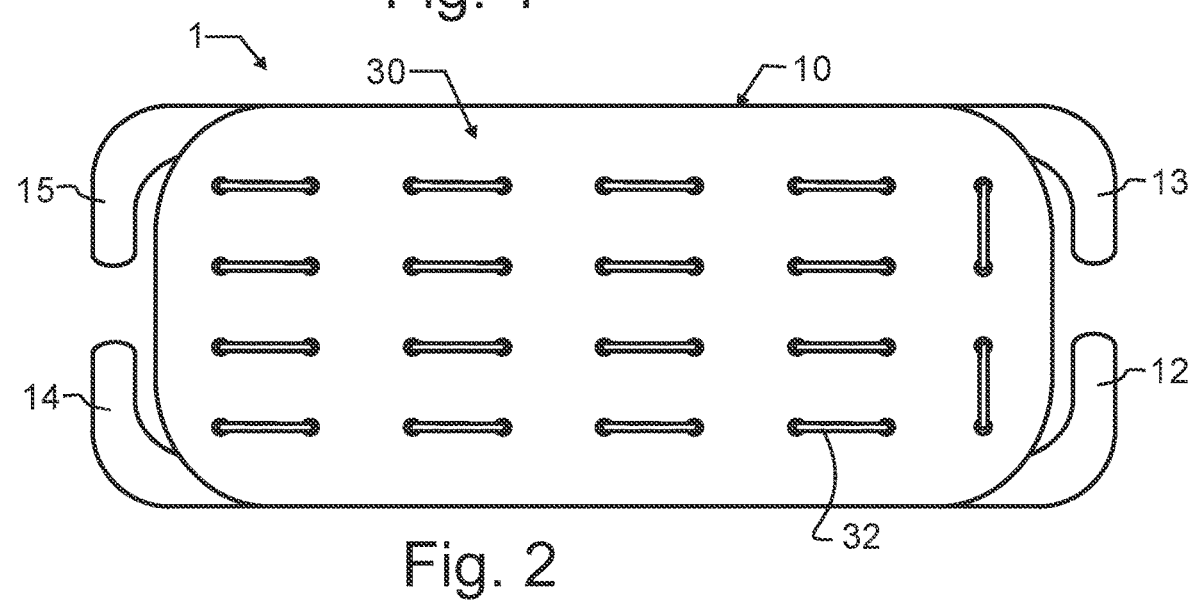
FIG. 2 illustrates the first preferred embodiment collar-mounted location sensor and stimulation unit of FIG. 1 from a top plan view.
Figure 3:
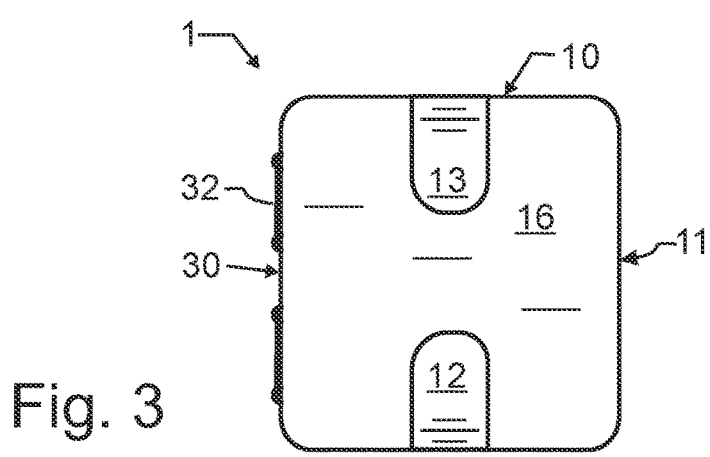
FIG. 3 illustrates the first preferred embodiment collar-mounted location sensor and stimulation unit of FIG. 1 from a side plan view.
Figure 5:
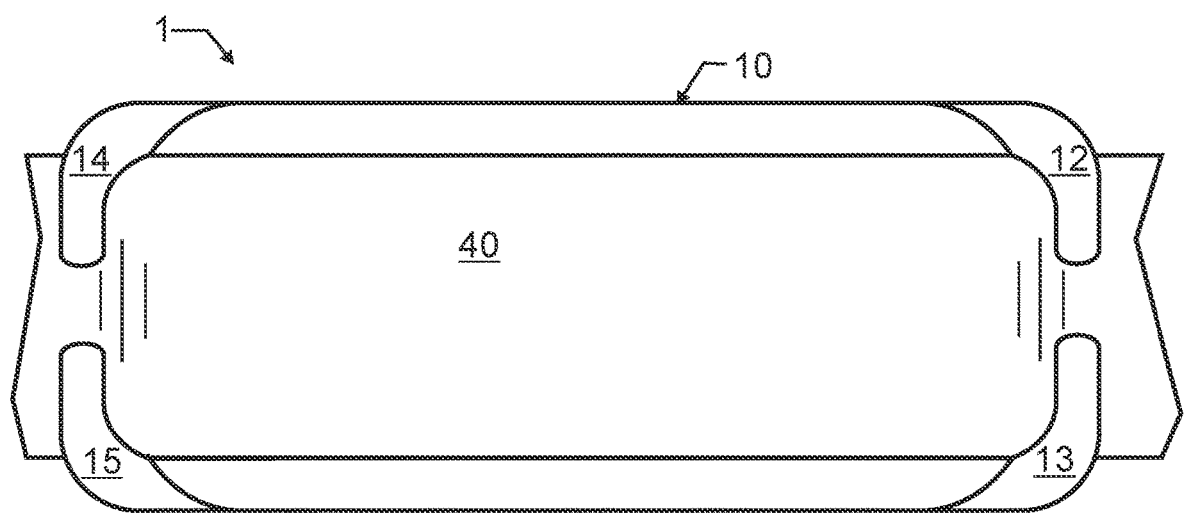
FIG. 5 illustrates the first preferred embodiment collar mount from bottom plan view of FIG. 1 and additionally affixed to a dog collar.

In a first preferred embodiment collar-mounted location sensor and stimulation unit 1, the body 10 is preferably generally rectangular, such as illustrated in FIG. 1. On each of the two short ends 16 and 17, two protrusions 12, 13 and 14, 15 respectively, called quick-mount retention clips, preferably extend from the superior and inferior lateral edges, bend in a 90 degree angle toward the center, and extend for a short distance before terminating, as illustrated in FIGS. 1-3. The first preferred embodiment collar-mounted location sensor and stimulation unit 1 is preferably slightly wider than a standard nylon dog collar, typically ¾" or 1" wide, as can be seen in FIG. 5. While not essential, the preferred embodiment collar-mounted location sensor and stimulation unit 1 is preferably not as thick as it is wide. It is preferably rounded on the long sides, and both rounded and tapered on the short sides, to avoid sharp edges that might over time abrade or harm a pet.

In the preferred embodiment collar-mounted location sensor and stimulation unit 1, the quick-mount retention clips 12-15 are fabricated from the same material as body 10 of the collar-mounted location sensor and stimulation unit 1. However, and where so desired, the quick-mount retention clips 12-15 may alternatively be fabricated from other suitable materials. For exemplary purposes, and not solely limiting thereto, the body and quick-mount retention clips 12-15 may be fabricated from a relatively stiff and rigid material that may range from a hard plastic to a relatively harder and stiffer elastomer or rubber-like material.

In an alternative embodiment, the body and quick-mount retention clips 12-15 may be fabricated from different materials. For exemplary purposes only, and not solely limiting thereto, the body 10 might be fabricated from a relatively stiff and rigid material, while the quick-mount retention clips 12-15 might be fabricated from a stiff but still pliable material such as an elastomer or rubber-like material. In a further alternative embodiment, the quick-mount retention clips 12-15 may be fabricated from a stiff inner core, and be provided with a more pliant and potentially more completely closed outer material.

Figure 4:
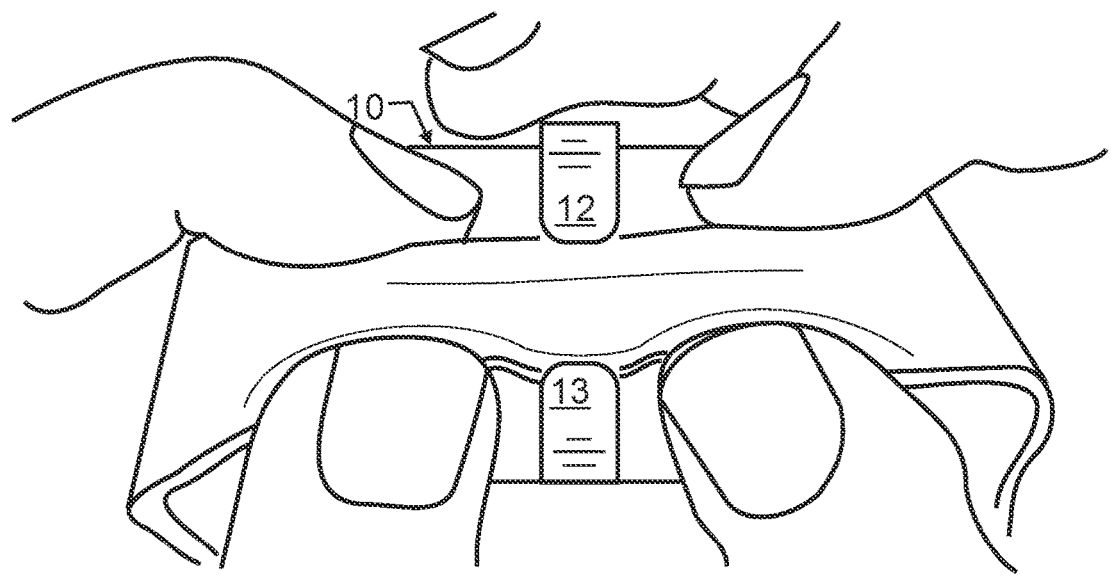
FIG. 4 illustrates the first preferred embodiment collar-mounted location sensor and stimulation unit of FIG. 1 from a side and slightly projected view during the collar installation process.

As can be seen in FIG. 5, when the preferred embodiment collar-mounted location sensor and stimulation unit 1 is affixed to a dog collar 40, the collar 40 is held in place by the quick-mount retention clips 12-15. Collar 40, if made of a flexible material such as nylon, leather and most other common collar materials, can operatively be pinched to fit in between the quick-mount clips 12-15 as illustrated in FIG. 4, then released to expand into normal shape within the space between the retention clips 12-15 and the ends 16, 17 of the collar-mounted location sensor and stimulation unit 1 to the position illustrated in FIG. 5. The use of more pliable materials for the quick-mount retention clips 12-15 will facilitate insertion, but will also increase the likelihood of separation of the collar-mounted location sensor and stimulation unit 1 from the collar 40. Consequently, in the preferred embodiment, the quick-mount retention clips 12-15 are fabricated from a rigid and stiff material.

The location sensor 20 and associated electronics are preferably encapsulated within or inset into the body of the collar-mounted location sensor and stimulation unit to protect them from potential damage. For exemplary and non-limiting purpose, suitable circuitry may incorporate components such as illustrated in US published patent application 2007/0204804 by Swanson et al incorporated by reference, suitably modified and configured to function for exemplary and non-limiting purpose as set forth in commonly owned U.S. Pat. Nos. 7,677,204; 9,795,118; 9,961,884; 10,064,390; 10,080,346; 10,165,755; 10,165,756; 10,172,325; 10,251,371; 10,292,365; 10,342,218; 10,405,520; 10,455,810; 10,470,437; 10,624,319; and 10,820,575.

Stimulation electrodes 32 will preferably be located on an inner face of the collar-mounted location sensor and stimulation unit 1 defined by coupling 30, adjacent to the dog when the collar is affixed on the dog. Coupling 30 is opposite to an outer face 11 visible in FIGS. 1 and 5. Collar 40 passes over outer face 11, and thereby urges body 10 and coupling 30 closer to a dog's hair or fur when secured.

Several preferred embodiments of apparatus and methods in accord with the present invention have been illustrated in the various figures. The embodiments are distinguished by the hundreds digit, and various components within each embodiment designated by the ones and tens digits. However, many of the components are alike or similar between embodiments, so numbering of the ones and tens digits have been maintained wherever possible, such that identical, like, or similar functions may more readily be identified between the embodiments. If not otherwise expressed, those skilled in the art will readily recognize the similarities and understand that in many cases like numbered ones and tens digit components may be substituted from one embodiment to another in accord with the present teachings, except where such substitution would otherwise destroy operation of the embodiment. Consequently, those skilled in the art will readily determine the function and operation of many of the components illustrated herein without unnecessary additional description.

Second preferred embodiment collar-mounted location sensor and stimulation unit 101 comprises a body 110 having an outer face 111, a set of quick-mount retention clips 112-115 protruding from each of the two short ends 116 and 117, and a location sensor 120 and associated electronics similar to those found in first preferred embodiment collar-mounted location sensor and stimulation unit 1. In addition thereto, second preferred embodiment collar-mounted location sensor and stimulation unit 101 has a pair of optional switches that are exemplary, though by no means limiting to the number, type, or placement of switches. These switches, including a select switch 122 and a cancel switch 124, may be provided to augment display 121 to facilitate entry of user selections into second preferred embodiment collar-mounted location sensor and stimulation unit 101. By providing these switches 122, 124 and display 121 on an inner face 131, they are accessible prior to installing second preferred embodiment collar-mounted location sensor and stimulation unit 101 onto an animal. On inner face 131, switches 122, 124 and display 121 are also relatively protected from damage or disturbance when an animal is wearing second preferred embodiment collar-mounted location sensor and stimulation unit 101.

As with first preferred embodiment collar-mounted location sensor and stimulation unit 1, and in similar manner, a suitable prior art dog collar 40 may be used to secure second preferred embodiment collar-mounted location sensor and stimulation unit 101 to the animal.

Figure 6:
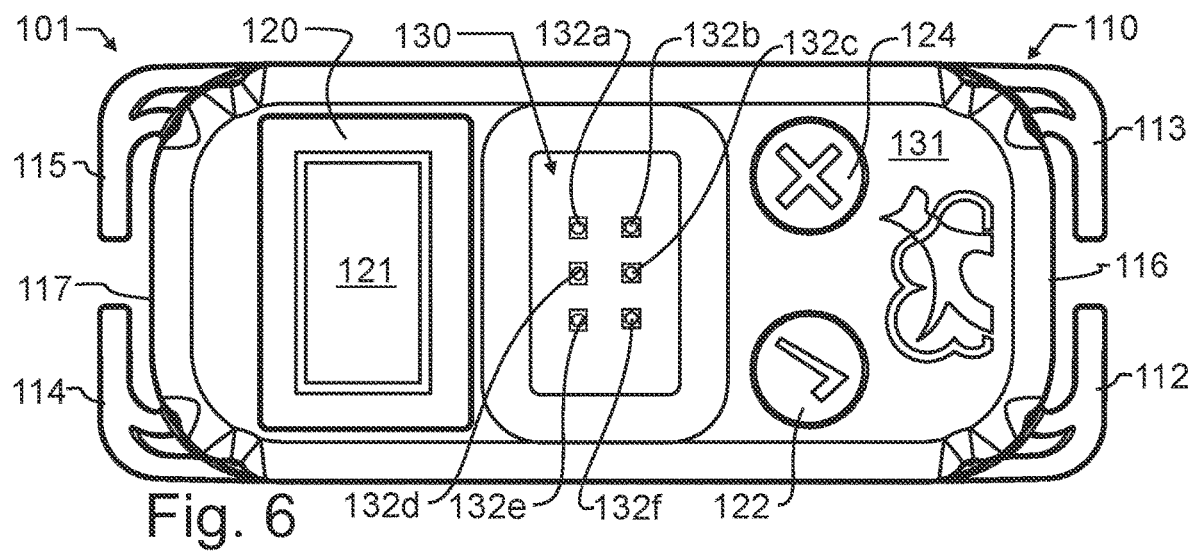
FIG. 6 illustrates a second preferred embodiment collar-mounted location sensor and stimulation unit from a bottom plan view designed in accord with the teachings of the present invention.

As visible in FIG. 6, electrodes 132a-f, like electrodes 32, are provided on a substantially flat coupling 130, and thereby define a generally planar electrode grid designed to make electrical contact with the hair or fur of an animal. This will be referred to herein as an exposed electrode sheet. The particular material used in the fabrication of electrodes 132a-f is not critical to the proper operation of the present invention, and so electrodes 132a-f may for exemplary and non-limiting purpose comprise conductive ink printed or otherwise patterned upon a substrate; pins inserted into holes within a substrate material; wires looped or otherwise installed within the substrate; or other suitable materials and configurations that provide adequate electrical conductivity.

While this electrode sheet defined by flat coupling 130 is in the preferred embodiments substantially planar, it will be understood from the present disclosure that such reference to planar may in some alternative embodiments be associated with a local arrangement. In these alternative embodiments, rather than the entire sheet being planar, the sheet may be gently curved to follow the rounded exterior geometry of a dog's neck while not significantly penetrating the fur, and for the purposes of the present disclosure will still be understood to be a sheet and to be substantially planar. In contrast, the prior art two-prong electrodes protrude substantially out of the surround support structure and are explicitly configured to penetrate through the dog's hair or fur.

In this second preferred embodiment collar-mounted location sensor and stimulation unit 101, coupling 130 is elevated slightly relative to inner face 131, which helps to ensure good contact between the relatively smaller grid defined by electrodes 132a-f and the animal's hair or fur, even if unit 101 were to be slightly tilted when engaged with the animal. Furthermore, the smaller surface area permits less collar force to be applied and still obtain adequate pressure to ensure good fur or hair contact. Nevertheless, the planar geometry of coupling 130 still ensures that electrodes 132a-f remain coupled with the animal hair or fur, and are not pressed through the fur into direct contact with the animal's skin.

Most preferably, electrodes 132a-f are provided in a grid or matrix with most nearly adjacent electrodes each having a differential voltage relative to each other. For exemplary purposes, if at a first moment in time electrode 132a is provided with a voltage of first magnitude, then the two closest electrodes 132b, d will be provided with a voltage of second magnitude different from the first. To complete this relationship, at this same first moment electrodes 132c, e will be provided with the voltage of first magnitude, and electrode 132f will be provided with the voltage of second magnitude. The substantially planar coupling 130 having alternating polarity electrodes better facilitates fur detection and electrical stimulation, even when second preferred embodiment collar-mounted location sensor and stimulation unit 101 is not resting evenly on the animal.

Figure 7:
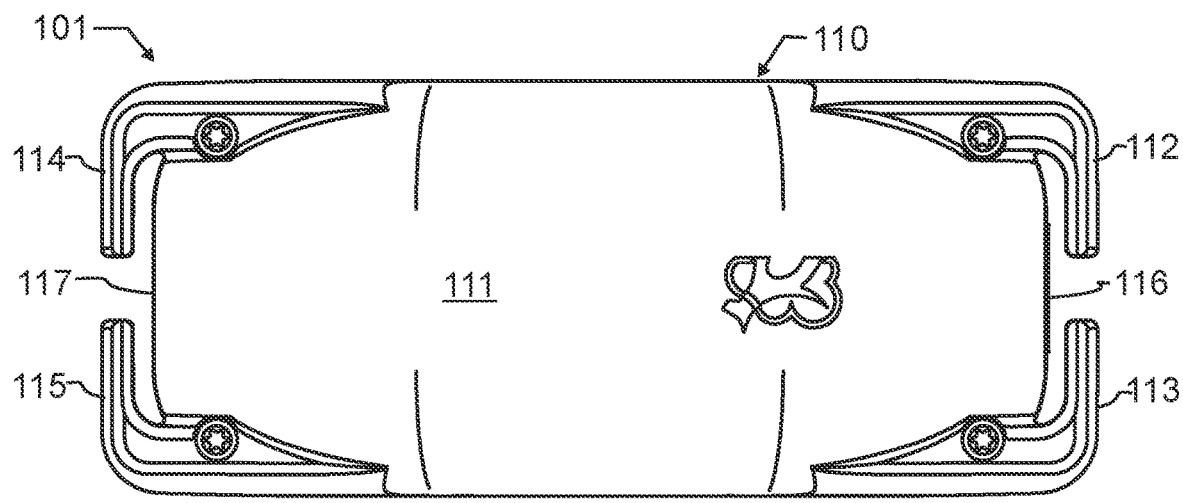
FIG. 7 illustrates the second preferred embodiment collar-mounted location sensor and stimulation unit of FIG. 6 from a top plan view.
Figure 8:
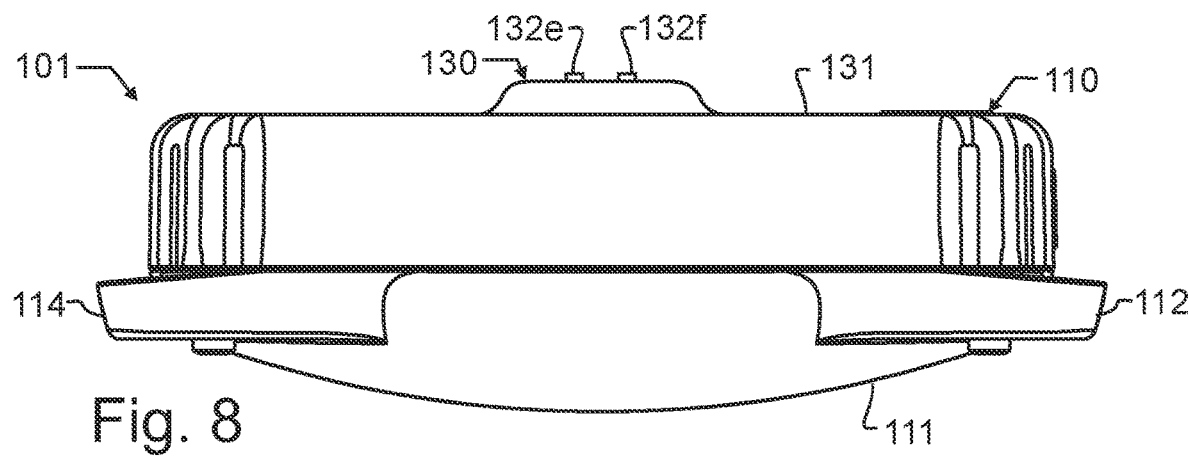
FIG. 8 illustrates the second preferred embodiment collar-mounted location sensor and stimulation unit of FIG. 6 from a side plan view.
Figure 9:
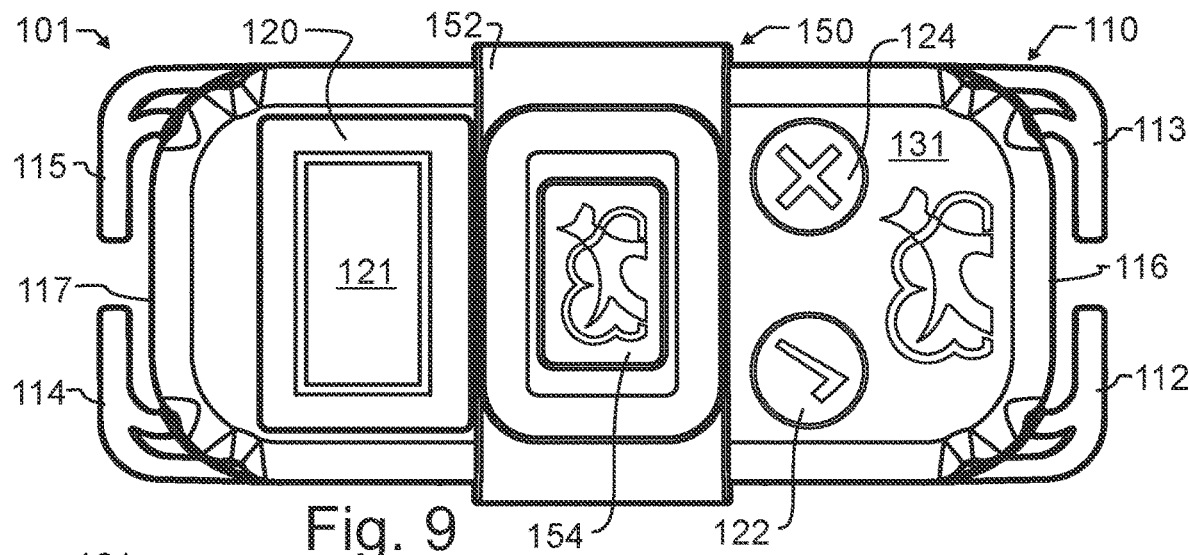
FIG. 9 illustrates a second preferred embodiment collar-mounted location sensor and stimulation unit of FIG. 6 from a bottom plan view, in further combination with an electrode cover.
Figure 10:
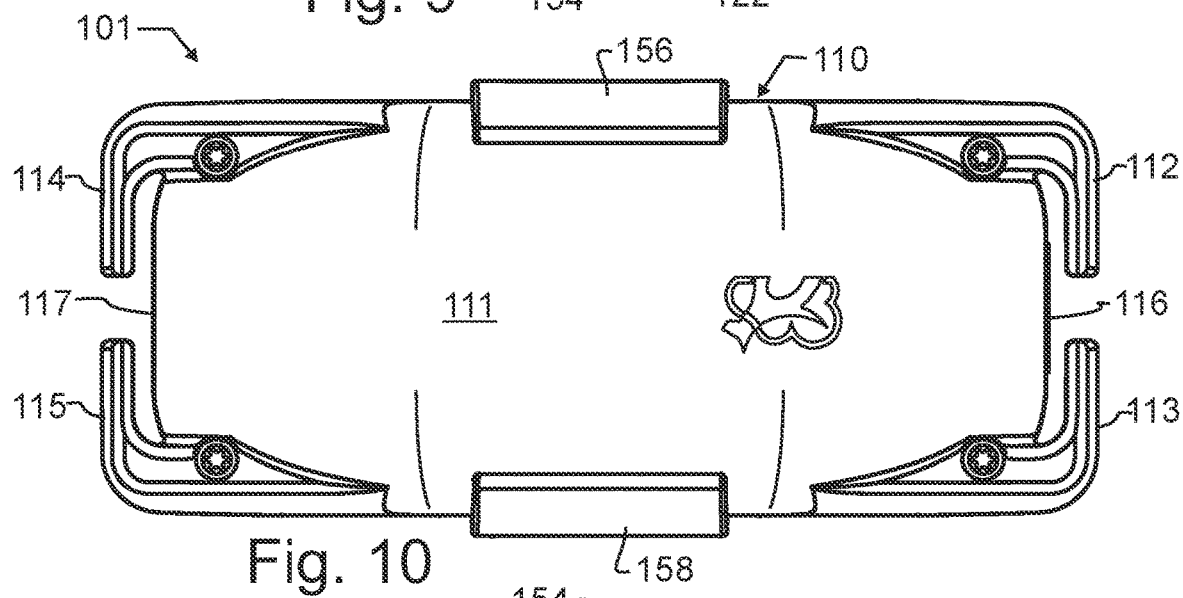
FIG. 10 illustrates the second preferred embodiment collar-mounted location sensor and stimulation unit of FIG. 9 from a top plan view.
Figure 11:
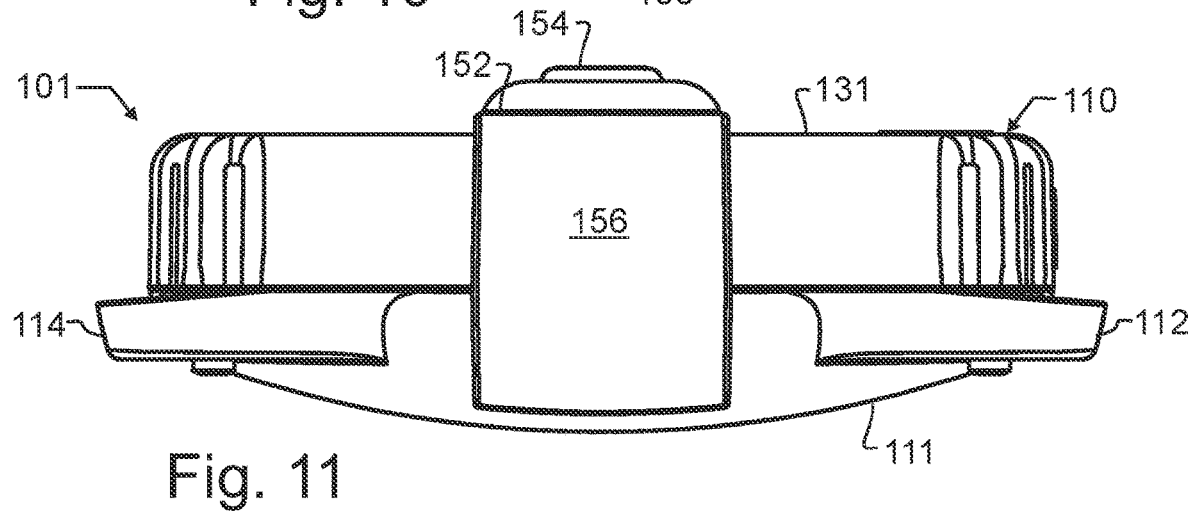
FIG. 11 illustrates the second preferred embodiment collar-mounted location sensor and stimulation unit of FIG. 9 from a side plan view.

In some instances, a user may prefer to forego electrical stimulation entirely. In such instances, and as illustrated in FIGS. 9-11, a user-removable cover 150 is provided that electrically isolates the electrodes from the animal. As will be understood, FIGS. 6-8 illustrate second preferred embodiment collar-mounted location sensor and stimulation unit 101 with cover 150 entirely removed, while FIGS. 9-11 illustrate cover 150 installed.

Cover 150 includes a cover base 152 from which rises an elevated electrode cover 154. Extending in an opposed direction from cover base 152 are a pair of "L"-shaped opposed cover securing clips 156, 158 that resiliently engage with outer face 111.

When a person turns on or initiates either first or second preferred embodiment collar-mounted location sensor and stimulation unit 1 or 101, the collar-mounted location sensor and stimulation unit 1, 101 may locate satellites and determine current location. In one alternative embodiment, the collar-mounted location sensor and stimulation unit 1, 101 may have a manual setting in order to activate or deactivate in order to save battery or to prevent stimulation at an undesired time.

However, in accord with the teachings of the present invention, the preferred embodiment collar-mounted location sensor and stimulation unit 1, 101 is provided with a sensor that is adapted to detect when the device is properly secured to a dog or other animal. For exemplary purposes, animal hair or fur presents a different capacitive input than open air. There is also a detectable difference between animal hair and human skin.

Figure 12:
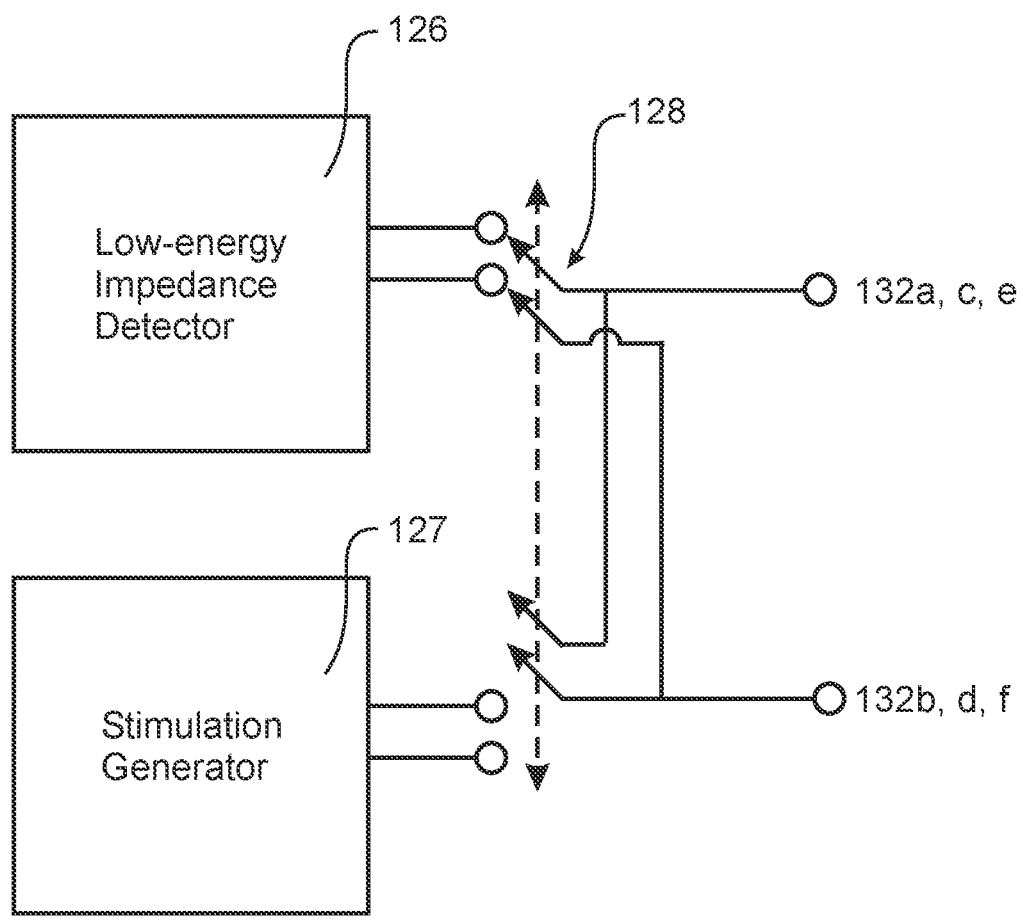
FIG. 12 illustrates an impedance detection apparatus in combination with a stimulation generator by simplified schematic diagram.

Consequently, in the preferred embodiments, the impedance is detected by the collar electronics using a low energy signal generated by low energy impedance detector 126. For the purposes of the present disclosure, this low energy signal will be understood to be a signal that is very close to or preferably below the detection threshold of the animal wearing the collar, and substantially below the threshold required in essentially any situation or skin, hair, or fur condition to cause the animal harm or to invoke tissue necrosis. As illustrated in FIG. 12, the signal is applied through a first shared signal line to electrodes 132a, c, and e, and through a second signal line to electrodes 132b, d, and f. In an alternative embodiment, a separate set of electrodes preferably in close proximity to electrodes 132a-f may be provided that are dedicated to coupling with the low energy signal generated by low energy impedance detector 126. In a further alternative embodiment, charging pins are provided to allow electrical connection to a charger that recharges the collar battery. In such case, these pins are electrically floating when the collar is in use and therefore separated from the charger, and so such pins may be used to detect fur impedance when not recharging the collar battery.

When an electrical signal is applied through electrodes 132a-f, those skilled in the electrical arts will recognize that the electrical characteristics being measured are sometimes referred to as complex impedance, meaning electrical resistance can also affect the results of a measurement. In some instances and cases, the awareness of electrical resistance can be highly beneficial in electrically characterizing the instantaneous nature of the skin, hair, or fur condition. However, and as may be appreciated then, when a transitory but extremely altering event such as a plunge in a salt-water body occurs, the skin, hair, and fur health and electrical characteristics may be so substantially altered for hours or days that electrical or computational analysis and interpretation of the complex impedance measurements can be difficult to conduct successfully.

Another measure of impedance, known as capacitance, can provide either better or different results or indications that may help interpret an observed electrical change. As a result, a capacitance measurement less influenced by resistance may provide insight, whether primary or cumulatively, into how an animal sensory stimulation apparatus should be altered to best protect the animal while preserving effective operation of the apparatus. In some embodiments, particularly where a dedicated set of electrodes are used for sensing capacitance, these electrodes may be provided with an electrical insulator such as plastic or other similar material. The electrical insulator material, which might for exemplary and non-limiting purposes comprise a very thin coating, film, or the like, will preferably inconsequentially change the capacitance, while preventing electrical resistivity from being detected.

In one particularly preferred embodiment of the invention, the capacitance measurement includes at least one electrode interior of a dielectric body 110, preferably located immediately adjacent to inner face 131. In such case, the electrode may be formed directly on or otherwise attached to the body 110 interior surface of inner face 131, or on a rigid circuit board or flex circuit located within the interior of body 110 and affixed directly to inner face 131. Body 110 acts as a long-term, highly reliable dielectric that will readily show any damage with simple visual inspection. In contrast, the very thin coatings, films, and the like mentioned herein above can be much more difficult to visually inspect.

In some alternative embodiments where thin dielectric coatings are applied, the electrode is fabricated from a material prone to substantial visual change if exposed conductively rather than capacitively directly to the exterior. Solely for exemplary and non-limiting purpose, materials such as silver and copper will oxidize or tarnish, though it will be understood that there are many metals and other coatings and compounds that can provide visual identification if the dielectric layer is damaged.

While in some embodiments capacitance is the preferred and primary method of detection, those familiar with the electrical arts will recognize that capacitance is one component of impedance, which also includes resistance and inductance. Consequently, in alternative embodiments alternative forms of impedance may alternatively or additionally be measured. Nevertheless, it is very desirable that such measurements provide sufficient specificity to distinguish animal hair or fur from alternative surfaces and from open air.

When an appropriate impedance is detected, this detection is used to determine that the preferred embodiment collar-mounted location sensor and stimulation unit 1, 101 is in place on an animal. Most preferably, in response to the detection of unique impedance, electrical switch 128 may be switched, and stimulation generator 127 may thereby be enabled. In addition to enabling stimulation generator 127, detection by low energy impedance detector 126 may also be used to enable other components within location sensor 120 and associated electronics. While a simple electrical switch 128 is illustrated, it will be appreciated that there are many well-known methods of enablement that can be used in various embodiments, including but not limited to various solid-state and opto-electronic switches. Further, while switch 128 is illustrated as either connecting low energy impedance detector 126 or stimulation generator 127 to electrodes 132a-f, depending upon circuitry selected in some alternative embodiments both apparatus are simultaneously connected, or, as noted herein above, they each may be connected to different electrode sets.

While even further alternative embodiments may employ other detection methods, such as a pressure sensor, optical detector or other suitable apparatus to determine when the collar-mounted location sensor and stimulation unit 1 is coupled to a pet, the unique capacitance presented by animal hair or fur allows the present invention to not only ensure the apparatus is not activated except when properly installed in contact with the animal hair or fur, but also to ensure that the preferred embodiment collar-mounted location sensor and stimulation unit 1, 101 will not unintentionally apply excessive energy or stimulation to an animal. This could, for exemplary and non-limiting purpose, occur in the prior art when a particular dog breed has greater conductivity than is normal, or might also for exemplary purposes occur when the collar is in place and the animal is doused with intrinsically electrically conductive liquids such as ocean or salt water, or other liquids that become electrically conductive when applied to the animal's hair or fur. Consequently, this initial impedance value will in some embodiments be used to calibrate or adjust one or more of a voltage, current, oscillation frequency, extent of modulation such as pulse-width modulation, or other suitable characteristics of an electrical signal applied to stimulation electrodes 32, 132a-f. In these embodiments, many factors including dog breed, seasonal fur thickness, and even daily variations in temperature, humidity, pet cleanliness and the like will be compensated for. In some embodiments, when different species are detectable, the stimulation output may further be adjusted accordingly. For exemplary and non-limiting purpose, human skin which is generally much more electrically conductive than dry dog fur may be identified, and in such instance the peak voltage may be much lower than dry dog hair or fur. Further, the behavior of the preferred embodiment collar-mounted location sensor and stimulation unit 1, 101 may also be adapted to correspond to the detected species, and as such may provide custom sequences or types of stimulation output that are more useful to the particular detected species.

As taught in commonly owned U.S. Pat. Nos. 9,795,118; 9,961,884; 10,064,390; and 10,080,346; the teachings which were incorporated herein above by reference, stimulation will most preferably first comprise auditory or vibratory stimulation, or some combination thereof. Nevertheless, when electrical correction is desired or required, such as when a pet leaves a designated area, preferred embodiment collar-mounted location sensor and stimulation units 1, 101 will preferably trigger an appropriate and non-adverse electrical stimulation. Most preferably, this electrical stimulation will be provided through couplings 30, 130 using electrodes 32 such as illustrated in commonly owned U.S. Pat. No. 7,677,204, the teachings and contents which are incorporated herein by reference, or the similar electrode grid 132a-f, which is considered to be a most humane method of application. This technology is designed to avoid tissue damage by providing non-necrotic stimulation. In addition, the technology illustrated in U.S. Pat. No. 7,677,204 works synergistically with the preferred quick-mount retention clips 12-15, since less force driving collar 40 into the dog is required for this stimulation technology to be effective.

To be most effective, in a most preferred embodiment the low energy impedance detector 126 will either remain connected, or will be intermittently switched in, to allow for regular testing to ensure that the correct impedance is present in advance of providing stimulation to an animal Consequently, if the dog is dry and outdoors, the fur will have an initial impedance value that the collar will detect. If there is rain, or if the dog ventures into water, then the fur or hair impedance may change significantly from that initially detected impedance. As the dog dries back out, the impedance may change again, perhaps drifting back toward the initial impedance value.

Based upon the detected impedance, a control system may then adjust one or more of a voltage, current, and even oscillation frequency of an electrical signal applied to stimulation electrodes 32, 132a-f. Many animals, including dogs, have sensory receptors such as mechanoreceptor nerves at the base of at least some of the hairs. These or other nerves in or just beneath the skin may be stimulated by the present invention. The present invention ensures consistent and either real-time or periodic calibration of output to provide a desired level of stimulation to the nervous system while protecting the animal from inhumane treatment or tissue damage.

Most preferably, impedance ranges acceptable to trigger electrical stimulation are defined that correspond in some embodiments to as little as one type or even breed of animal. In other embodiments, these acceptable impedance ranges will correspond to a wider variety of breeds, or in yet other embodiments a plurality of animal species.

To further refine the identification of skin, hair, and fur health and electrical characteristics, in some embodiments at least two types of impedance detection are used. For exemplary and non-limiting purpose, in such embodiments a first assessment of impedance is conducted using a capacitance detection. A second assessment of complex impedance having the possibility of greater affect due to resistance is immediately or very shortly thereafter conducted using direct connection to electrodes 132a-f. The present invention is not limited to two specific impedance tests. In some embodiments, further tests may be required or desired to further characterize animal skin, hair, and fur health and electrical characteristics, such as by varying frequency, voltage, pulse width, duty-cycle, or other test signal characteristic.

In some embodiments, this second or any subsequent assessment is only conducted when the first or earlier impedance detections are out of an expected range. The expected range may be based on long-term historical data obtained during use of the animal sensory stimulation apparatus with a single animal, or may be relatively more short term, potentially even due to substantial deviation between temporally adjacent measurements. For exemplary and non-limiting purpose, such deviations might arise when an animal is unexpectedly doused in sea water, or may be due to a collar being accidentally or intentionally removed. In some other embodiments, the second assessment is always conducted.

While the foregoing details what are felt to be the preferred and additional alternative embodiments of the invention, no material limitations to the scope of the claimed invention are intended. The variants that would be possible from a reading of the present disclosure are too many in number for individual listings herein, though they are understood to be included in the present invention. For exemplary purposes only, and not solely limiting the invention thereto, the words "dog" and "animal" have been used interchangeably herein above. This is in recognition that the present invention has been designed specifically for use with dogs, but with the understanding that other animals may also be trained using apparatus in accord with the teachings of the present invention. Consequently, the present invention is understood to be applicable to other animals, and the differences that will be required of an alternative embodiment designed for animals other than dogs will be recognized based upon principles that are known in the art of animal training. Further, features and design alternatives that would be obvious to one of ordinary skill in the art are considered to be incorporated herein. The scope of the invention is set forth and particularly described in the claims herein below.

I claim:

1. A collar-mounted animal sensory stimulation unit with fur differential impedance detection, comprising:
    a body supporting at least one exposed stimulation electrode and at least one dielectrically isolated electrode;
    an electrical stimulation generator having an electrical stimulation output electrically coupled to said at least one exposed stimulation electrode;
    an impedance detector electrically coupled to said at least one exposed stimulation electrode and said at least one dielectrically isolated electrode and configured to detect exposed electrode impedance through said at least one exposed stimulation electrode and measure capacitance at least through said at least one dielectrically isolated electrode;
    said electrical stimulation generator configured to alter said electrical stimulation output responsive to said detected exposed electrode impedance and said measured capacitance.

2. The collar-mounted animal sensory stimulation unit with fur differential impedance detection of claim 1, further comprising a location sensor configured to determine a location of said body, said electrical stimulation generator configured to alter said electrical stimulation output responsive to said determined body location.

3. The collar-mounted animal sensory stimulation unit with fur differential impedance detection of claim 2, wherein said impedance detector is configured to detect said exposed electrode impedance and said capacitance prior to activation of said electrical stimulation generator, said electrical stimulation generator configured to alter said electrical stimulation output responsive to said detected exposed electrode impedance and said measured capacitance and responsive to a deactivation of said electrical stimulation generator followed by an activation of said electrical stimulation generator repetitively detected magnitude of impedance.

4. The collar-mounted animal sensory stimulation unit with fur differential impedance detection of claim 1, wherein said impedance detector further comprises a detector generating a low-energy signal below a dog stimulation threshold.

5. The collar-mounted animal sensory stimulation unit with fur differential impedance detection of claim 1, wherein said at least one dielectrically isolated electrode comprises an electrode dielectrically isolated by said body.

6. The collar-mounted animal sensory stimulation unit with fur differential impedance detection of claim 1, further comprising at least one sensory stimulator configured to provide at least one of auditory, kinesthetic, and visual stimulation to said dog responsive to an output of said location sensor.

7. A method of providing electrical animal sensory stimulation through animal fur responsive to differential impedance detection, comprising the steps of:
    electrically coupling stimulation electrodes to said animal fur;
    measuring impedance between said stimulation electrodes;
    electrically coupling at least one dielectrically isolated electrode to said animal fur;
    measuring capacitance of said animal fur through said at least one dielectrically isolated electrode;
    determining said measured impedance and capacitance represents that said stimulation electrodes are coupled to said animal fur;
    applying electrical stimulation through said stimulation electrodes to said animal fur responsive to said determining step, and
    extinguishing said electrical stimulation through said stimulation electrodes to said animal fur absent said determining step represents that said stimulation electrodes are coupled to said animal fur.

8. The method of providing electrical animal sensory stimulation through animal fur responsive to differential impedance detection of claim 7, wherein said stimulation electrodes comprise a generally planar sheet having a plurality of stimulation electrodes pressed against said animal fur.

9. The method of providing electrical animal sensory stimulation through animal fur responsive to differential impedance detection of claim 7, wherein said measuring step further comprises the step of transmitting an electrical measuring signal having a low-energy signal below a dog stimulation threshold through said stimulation electrodes.

10. The method of providing electrical animal sensory stimulation through animal fur responsive to differential impedance detection of claim 7, further comprising the step of covering said stimulation electrodes with an electrode cover and thereby isolating said stimulation electrodes from said animal fur.

11. The method of providing electrical animal sensory stimulation through animal fur responsive to differential impedance detection of claim 7, further comprising the step of repeating said steps of measuring, determining, applying, and extinguishing.

12. The method of providing electrical animal sensory stimulation through animal fur responsive to differential impedance detection of claim 7, further comprising the steps of:

establishing a geo-position-based location of said stimulation electrodes;

selectively providing auditory, kinesthetic, and visual stimulation to said dog responsive to said geo-position-based location establishing step.

13. The method of providing electrical animal sensory stimulation through animal fur responsive to differential impedance detection of claim 7, further comprising the step of repeating said steps of establishing and selectively providing.

14. A method of providing electrical animal sensory stimulation through animal fur responsive to differential impedance detection, comprising the steps of:

electrically coupling stimulation electrodes to said animal fur;

detecting a magnitude of impedance between said stimulation electrodes;

electrically coupling at least one dielectrically isolated electrode to said animal fur;

measuring capacitance of said animal fur through said at least one dielectrically isolated electrode;

varying an output of an electrical stimulation generator responsive to said detected magnitude of impedance and said measured capacitance; and applying said electrical animal sensory stimulation through said electrical stimulation electrodes to said animal fur subsequent to said output varying step.

15. The method of providing electrical animal sensory stimulation through animal fur responsive to differential impedance detection of claim 14, wherein said stimulation electrodes comprise a generally planar sheet having a plurality of stimulation electrodes pressed against said animal fur.

16. The method of providing electrical animal sensory stimulation through animal fur responsive to differential impedance detection of claim 14, wherein said detecting step further comprises the step of transmitting an electrical measuring signal having a low-energy signal below a dog stimulation threshold through said stimulation electrodes.

17. The method of providing electrical animal sensory stimulation through animal fur responsive to differential impedance detection of claim 14, further comprising the steps of:

establishing a geo-position-based location of said stimulation electrodes;

selectively providing auditory, kinesthetic, and visual stimulation to said dog responsive to said geo-position-based location establishing step.

18. The method of providing electrical animal sensory stimulation through animal fur responsive to differential impedance detection of claim 17, further comprising the step of repeating said steps of establishing and selectively providing.

* * * * *